US00PP21450P2

(12) United States Plant Patent
Rowling et al.

(10) Patent No.: US PP21,450 P2
(45) Date of Patent: Nov. 9, 2010

(54) APPLE TREE, 'MOANA'

(50) Latin Name: Malus domestica Mil
Varietal Denomination: Moana

(75) Inventors: Geoff Rowling, Upper Moutere (NZ); Alan Rowling, Upper Moutere (NZ)

(73) Assignee: Moana Orchards Ltd. (NZ)

( * ) Notice: Subject to any disclaimer, the term of this patent is extended or adjusted under 35 U.S.C. 154(b) by 0 days.

(21) Appl. No.: 12/454,082

(22) Filed: May 11, 2009

(51) Int. Cl.
*A01H 5/00* (2006.01)

(52) U.S. Cl. ..... Plt./168

(58) Field of Classification Search ..... Plt./168
See application file for complete search history.

(56) References Cited

U.S. PATENT DOCUMENTS

PP17,914 P2 8/2007 Lee et al. ..... Plt./168
PP18,661 P2 3/2008 Austin ..... Plt./168

*Primary Examiner*—June Hwu
(74) *Attorney, Agent, or Firm*—Wells St. John P.S.

(57) ABSTRACT

A new and distinct variety of apple tree 'Malus domestica Mil' named 'Moana' is described and which is characterized by a date of maturity of April 15th or later under the ecological conditions prevailing near Nelson, New Zealand.

2 Drawing Sheets

BACKGROUND OF THE NEW VARIETY

The present invention relates to a new and distinct variety of apple tree, 'Malus domestica Mil', and which is denominated varietally as 'Moana,' and more particularly to an apple tree which bears a distinctive and attractively colored round apple having a firm and crisp flesh texture and which further can be stored for commercially acceptable periods of time with little deterioration in the overall quality of the fruit.

ORIGIN AND ASEXUAL REPRODUCTION

It has long been recognized that a very important factor contributing to the success of any variety of apple tree bearing fruit for the fresh market is its ability to produce an attractively colored fruit which has good handling characteristics, and a distinctive flavor. The new variety 'Moana' is noteworthy, and distinguishable from the varieties it is most closely similar to, in producing an attractively and distinctly colored fruit having a skin color which is about 95% to 100% solid red flush, and which further has an attractive globose shape. The new variety is harvested during the same season where other known, and closely similar varieties such as the 'Nagafu-6' (unpatented) apple tree; 'Candy' (U.S. Plant Pat. No. 18,661); 'CABp' Fuji (U.S. Plant Pat. No. 17,914); and the apple tree variety 'DT2,' often referred to as the 'Aztec Fuji'™ (unpatented), are harvested, and under the ecological conditions prevailing in Upper Moutere, Nelson, New Zealand.

The new variety of apple tree, 'Moana' was discovered as a limb sport mutation of a 'Nagafu-6' (unpatented) Fuji apple tree which was then growing in a cultivated orchard controlled by the inventors, and which is located at Upper Moutere, Nelson, New Zealand in May, 1996, during routine orchard operations. The inventors recognized the novel characteristics of the new variety of apple tree and then marked it for subsequent observation. Thereafter, the inventors removed bud wood from the chance sport and grafted it into several test trees growing in the same orchard. This first asexual reproduction of the variety occurred during October, 1998. The new variety 'Moana' has been observed since that time, and the first fruit was produced from these asexually reproduced trees and evaluated during April-May, 2001. Following confirmation that the fruit produced by these first asexually reproduced trees were true to the original chance sport, more bud wood was removed from the original sport and grafted over to production trees then growing in the same orchard in October, 2001. Fruit produced by these subsequent asexually reproduced trees have been evaluated and are true to the fruit produced by the original chance sport. All subsequent asexual reproductions have confirmed the unique characteristics of this new apple tree.

The present variety 'Moana' is readily distinguishable from the 'Nagafu-6' (unpatented) Fuji apple tree from which it was derived as a chance sport by producing a globose shaped fruit having a skin color which is about 95% to 100% solid red flush. In relative comparison, the fruit produced by the 'Nagafu-6' (unpatented) Fuji apple tree produces fruit having a skin color which is about 30-40% solid red flush with some weak stripes. Further, the new variety is distinguishable from other closely related varieties such as the 'Candy' apple tree (U.S. Plant Pat. No. 18,661) and which produces fruit having a skin color which is about 90-100% solid red flush with prominent stripes; and the fruit of the 'DT2' (unpatented) Fuji apple tree which has a skin color which has a solid red flush with weak stripes. Further, 'CABp' Fuji apple tree (U.S. Plant Pat. No. 17,914) produces fruit having a skin color which is about 50-66% solid red flush and which has more prominent striping (95%-100%).

SUMMARY OF THE VARIETY

The 'Moana' apple tree is characterized principally as to novelty by producing a unique, attractively colored, globose shaped apple which is ripe for harvesting and shipment about April 15 through early May, under the ecological conditions prevailing in Upper Moutere, Nelson, New Zealand.

BRIEF DESCRIPTION OF THE DRAWINGS

The accompanying drawings are color photographs of the present variety. These photographs depict the whole fruit as would be seen on a typical branch of a tree, and the flowering characteristics of the new variety. These colors are as nearly true as reasonably possible with a color reproduction of this type. Due to chemical development, processing and printing, the leaves and fruit depicted in these photographs may or may not be accurate when compared to the actual specimen. For this reason, future color references should be made to the color plates (Royal Horticulture Society Colour Chart), and descriptions provided hereinafter. Occasionally common color names will also be used.

NOT A COMMERCIAL WARRANTY

Figure 1:
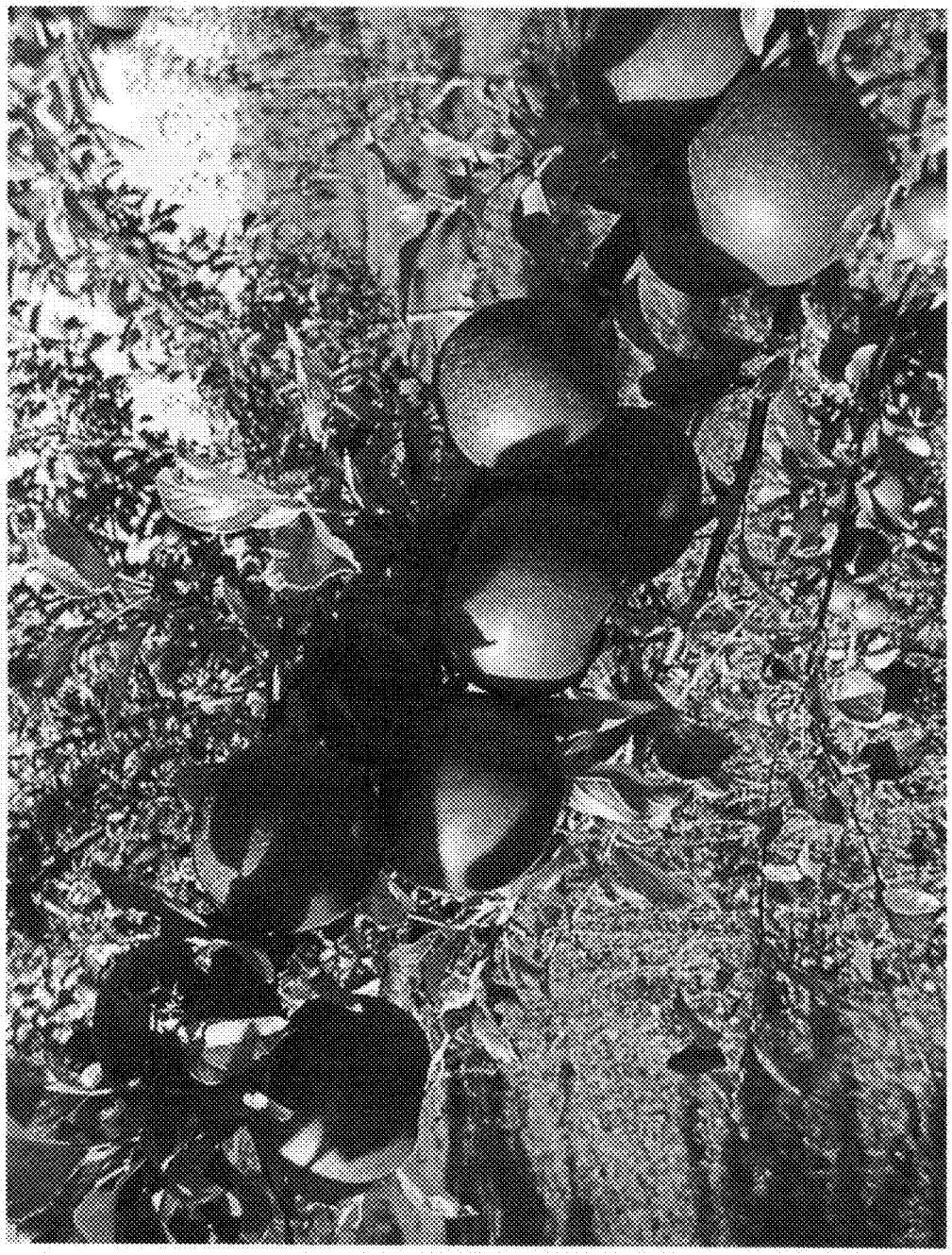
FIG. 1 shows the fruiting habit of the present variety. The apples as seen in this photograph are sufficiently matured for harvesting and shipment.
Figure 2:
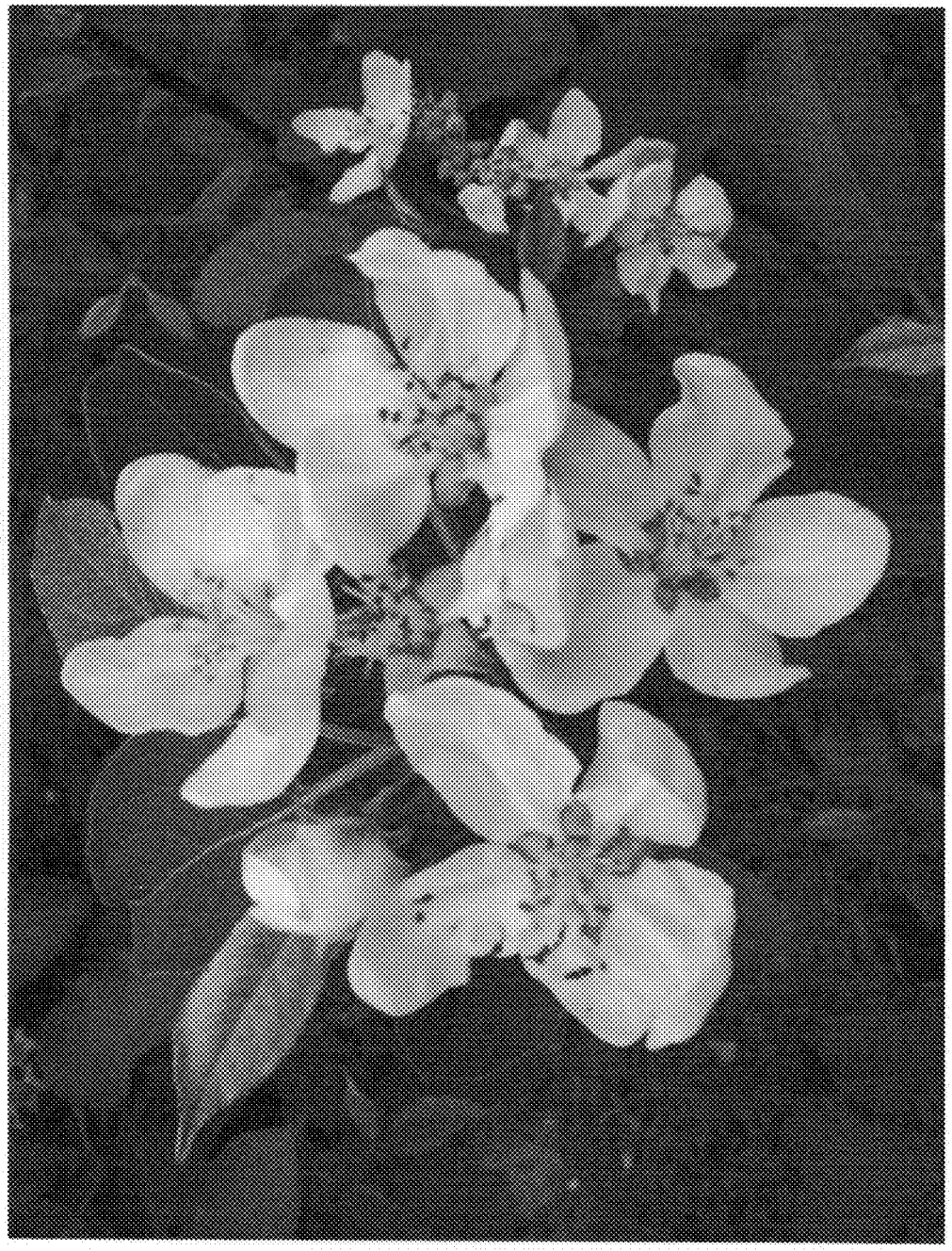
FIG. 2 depicts the flowering characteristic of the present novel apple tree.

The following detailed description has been prepared to solely comply with the provisions of 35 USC §112, and does not constitute a commercial warranty (either expressed or implied), that the present variety will, in the future, display the botanical or other varietal characteristics as set forth in this application. Therefore, this disclosure may not be relied upon to support any legal claims, which include, but are not limited to breach of warranty of merchantability, fitness for any particular purpose, or non-infringement which is directed in whole, or in part, to the present variety.

DETAILED DESCRIPTION

Referring more specifically to the pomological details of this new and distinct variety of apple tree, the following has been observed under the ecological conditions prevailing at the orchard of the inventors which is located near Nelson, New Zealand. All major color code designations are by reference to The R.H.S. Colour Chart, 4th Edition provided by The Royal Horticulture Society of Great Britain.

Tree:

- *Size.*—Considered average for the species.
- *Height.*—About 4 meters. Crown diameter — about 3.5 meters when measured at a height of about 1 meter above the surface of the earth. These measurements were taken from trees which were about 7 years old.
- *Vigor.*—Average for the species.
- *Tree type.*—Ramified.
- *Growth habit.*—Considered spreading; Tree Bearing: Mixed containing both spurs and long shoots.

Trunk:

- *Size.*—Considered average for the species.
- *Diameter.*—About 11 cm. when measured at a distance of about 20 cm. above the graft union.
- *Bark texture.*—Considered smooth.
- *Bark color.*—Grey-green (RHS 197D).
- *Bark lenticels.*—Size — About 9 mm. long, and about 1 mm. wide.
- *Bark lenticel color.*—Grey-yellow (RHS 161A).
- *Lenticel density.*—About 5 lenticels per square cm.

Branches:

- *Size.*—About 32 mm. in diameter when measured on 4 year old branches which are located about 50 cm. from the main trunk.
- *Crotch angle.*—Variable from about 20 degrees below, to about 40 degrees above horizontal.
- *Branch color.*—Grey-brown (RHS 199A).
- *Lenticels.*—Size — About 4 mm. long, and about 1 mm. wide.
- *Lenticel color.*—Grey-yellow (RHS 161A).
- *Lenticel density.*—About 9 lenticels per square cm.
- *Hardiness.*—Considered hardy under the current ecological conditions as experienced in Nelson, New Zealand.
- *Chilling requirement.*—Considered similar to that required for other patented and unpatented varieties of 'Fuji' apple trees growing in the same geographical area.
- *One year old growth.*—Size — Considered average for the variety. About 40 cm. in length, and about 5 mm. in diameter.
- *One year old growth.*—Surface texture — Considered moderately pubescent.
- *One year old growth.*—Surface color — Grey-orange (RHS 174A).
- *One year old growth.*—Internode length — About 3 to about 3.5 cm.
- *One year old growth.*—Pubescence — Present, and considered medium for the variety.

Flowers:

- *Flower buds.*—Numbers — Typically, 1 per spur will be found.
- *Flower buds.*—Shape — Considered pointed.
- *Flower buds.*—Length — About 8.5 mm.
- *Flower buds.*—Diameter — About 4.1 mm.
- *Flower buds.*—Color — Grey (RHS 201C).
- *Flower size.*—About 38 mm. when fully opened.
- *Flowers per cluster.*—5 or 6 flowers will typically be found.
- *Flower petals.*—Generally — 5 flower petals will typically be found in each flower.
- *Flower petal orientation.*—The flower petals are touching.
- *Flower petal length.*—About 22 mm.
- *Flower petal width.*—About 12 mm.
- *Flower petal apex.*—Generally speaking, the apex shape is rounded.
- *Flower petal marginal form.*—Considered smooth.
- *Flower petals.*—Upper Surface Color — Predominately white (RHS 155C).
- *Flower petals.*—Lower Surface Color — The lower surface of the flower petal has faint staining of a red-purple color (RHS 73B) when the flower is fully opened.
- *Sepals.*—Length — About 5 mm.
- *Sepals.*—Width — About 2 mm.
- *Sepal color.*—Green (RHS 145A).
- *Pedicel.*—Length — About 29 mm.
- *Stamens.*—Number — Numerous. The number of stamens is not distinctive of the present variety.
- *Anthers.*—Length — About 5 mm.
- *Anthers.*—Color — Yellow (RHS 11C).
- *Pistil.*—Length — About 8 mm. Only one pistil is found per flower.
- *Pistil.*—Color — Green (RHS 145C).
- *Flowering time.*—Considered average for the variety. In 2008, full bloom was achieved on 14 October under the ecological conditions prevailing near Nelson, New Zealand.
- *Pollination.*—Any diploid cultivar other than a Fuji or Fuji sport which flowers at a similar time can serve as an adequate pollinizer for 'Moana.'

Leaves:

*Leaf orientation relative to the shoot.*—Considered upwardly oriented.

*Leaf length.*—On average about 79 mm. when measured on 1 year old shoots. Leaf Stipules — Shape — Lanceolate; Leaf Stipules — Width — about 2.5 mm; Leaf Stipules Length — about 8.3 mm.

*Leaf width.*—About 47 mm., on average.

*Leaf shape.*—Considered ovate.

*Apex shape.*—Acuminate.

*Base.*—Shape — Obtuse.

*Marginal form.*—Considered crenate.

*Upper leaf color.*—Yellow-green (RHS 147A).

*Lower leaf color.*—Green (RHS 138B).

Fruit:

*Size at commercial maturity.*—Considered large and having a height of about 69 mm. and a diameter of about 80 mm.

*Fruit weight.*—On average at commercial maturity, the respective fruit weighs about 200 grams. This is not distinctive of the present variety because fruit weight can be so easily effected by prevailing cultural practice and ambient environmental conditions.

*Fruit shape when considered in profile.*—Globose.

*Position of maximum fruit diameter.*—Approximately the middle of the fruit.

*Fruit ribbing.*—Not detected.

*Aperture of eye.*—Considered closed.

*Size of the eye.*—Considered small for the species. Locules — Number — 5; Locule Width — about 11.7 mm.; Locule Depth — about 5.2 mm.; Locule Length — about 13.2 mm.

*Eye basin.*—Size — About 10 mm. in depth and about 25 mm. in width.

*Stalk.*—Size — About 2 mm. in diameter, and having a length of about 22 mm.

*Stalk.*—Color — Grey-brown (RHS 199A).

*Stalk cavity.*—Size — About 14 mm. in depth and about 29 mm. wide.

*Lenticels.*—Size — Considered medium to large for the species; Lenticel Density — about 4 per square centimeter.

*Skin bloom.*—Generally — Considered present.

*Skin greasiness.*—Absent.

*Ground color of the Skin.*—Yellow-green (RHS 154C).

*Skin over color.*—Grey-purple (RHS 185A).

*Over color pattern.*—Solid flush.

*Over color.*—Amount — Considered high, about 95% to about 100%.

*Russet.*—Generally — When considered around the eye basin, it is absent or very low. Further, the russet on the cheeks is considered low to moderate for the species. A moderate amount of russet is found in the vicinity of the stalk cavity.

*Fruit flesh.*—Texture — Considered average, firm and crisp and having a fruit pressure at about 6.5 kg. to about 7 kg; Brix — about 13.

*Flesh color.*—White (RHS 155B).

*Seed numbers.*—9 per fruit will be found; Seed Size—about 9.4 mm. long and about 4.9 mm. wide.

*Seed color.*—Grey-orange (RHS 166A).

*Maturity for commercial harvesting and shipment.*—About April 15-April 30 under the ecological conditions prevailing near Nelson, New Zealand.

*Fruit use.*—A fresh fruit apple for local and long distance markets; Fruit Aroma — Considered sweet.

*Fruit storage.*—Similar to that experienced by the various commercially available 'Fuji' cultivars.

*Resistance to diseases.*—No particular susceptibilities were noted.

Although the new variety of apple tree herein denominated as 'Moana' possesses the described characteristics when grown under the ecological conditions prevailing near Nelson, New Zealand, it is to be understood that variations of the usual magnitude and characteristics incident to changes in growing conditions, fertilization, pruning and pest control are to be expected.

Having thus described and illustrated our new variety of apple tree, what we claim is new, and desire to secure by Plant Letters Patent is:

1. A new and distinct variety of apple tree substantially as illustrated and described and which is mature for harvesting and shipment on or after April 15$^{th}$ under the ecological conditions prevailing near Nelson, New Zealand.

* * * * *